United States Patent [19]
Leigh

[11] Patent Number: 5,840,315
[45] Date of Patent: Nov. 24, 1998

[54] VACCINES BASED ON STREPTOKINASE

[75] Inventor: James Andrew Leigh, Newbury, England

[73] Assignee: Pfizer Inc., New York, N.Y.

[21] Appl. No.: 256,632

[22] PCT Filed: Jan. 18, 1993

[86] PCT No.: PCT/GB93/00110

§ 371 Date: Jul. 15, 1994

§ 102(e) Date: Jul. 15, 1994

[87] PCT Pub. No.: WO93/14209

PCT Pub. Date: Jul. 22, 1993

[30] Foreign Application Priority Data

Jan. 17, 1992 [GB] United Kingdom .................. 9201013

[51] Int. Cl.⁶ .................................................. A61K 39/09
[52] U.S. Cl. .................................. 424/244.1; 424/234.1; 424/243.1; 530/350; 435/68.1; 435/69.2; 435/216
[58] Field of Search ............................. 424/244.1, 243.1, 424/823; 530/350, 825; 435/216, 68.1, 69.2

[56] References Cited

U.S. PATENT DOCUMENTS

| 4,021,541 | 5/1977 | Lange et al. | |
|---|---|---|---|
| 4,675,176 | 6/1987 | Gerber | 424/88 |
| 5,198,215 | 3/1993 | De Cueninck | 424/92 |

FOREIGN PATENT DOCUMENTS

| 0 094 997 | 11/1983 | European Pat. Off. . |
|---|---|---|
| 0 407 942 | 1/1991 | European Pat. Off. . |
| 8 606 634 | 11/1986 | WIPO . |
| 9 011 367 | 10/1990 | WIPO . |

OTHER PUBLICATIONS

Chemical Abstracts vol. 66, 1967 Colombus, Ohio, US abstract no. 72476 p. 6787, col. 2 see abstract.
J Biol Chem vol. 242, No. 7, 1967 pp.1419–1425.
Chemical Abstracts vol. 74, 1971 Colombus, Ohio, US abstract no.85130 pp. 197, col 1 see abstract.
J Biol Chem vol. 245, No. 23, 1970 pp. 6389–6396.
Chemical Abstracts vol. 88, 1978 Colombus, Ohio, US abstract no. 149686 p. 366, col. 1 see abstract.
J Biol Chem vol. 253, No. 5, 1978 pp. 1402–1407.
Chemical Abstracts vol. 85, 1976 Colombus, Ohio, US abstract no. 75661 p. 353, col. 1 see abstract.
Research in Veterinary Science vol. 49, 1990, Oxford UK, pp. 85–87.
Verdi et al J. Dairy Science 74:772–782, 1991.
Coffin et al J. Dairy Science 66:2161–2166, 1983.
Ling et al J. Biol. Chem 242(7) :1419–1425, 1967.
Leigh et al Research in Vet. Science. 1990. 49: 85–87.

*Primary Examiner*—James C. Housel
*Assistant Examiner*—Jennifer Shaver
*Attorney, Agent, or Firm*—Peter C. Richardson; Paul H. Ginsburg; Alan L. Koller

[57] ABSTRACT

The present invention provides a vaccine to treat or prevent mastitis in a bovine species, comprising an immunologically effective amount of a plasminogen-activating streptokinase protein produced by *Streptococcus uberis*. The present invention further provides a method of treating or preventing mastitis in a bovine species comprising vaccinating a cow with an immunologically effective amount of a plasminogen-activating streptokinase protein produced by *S. uberis*. The present invention further provides an isolated plasminogen-activating streptokinase protein produced by *S. uberis*, or an immunogenic fragment thereof.

4 Claims, 5 Drawing Sheets

VACCINES BASED ON STREPTOKINASE

This application is the U.S. national stage of PCT/GB93/00110, filed Jan. 18, 1993, which International Application claims priority Great Britain application No. 9201013.1 filed Jan. 17, 1992.

This invention relates to vaccination against diseases caused by pathogens, and more particularly to vaccination against mastitis.

To cause clinical mastitis in the bovine udder a bacterium must either grow within the gland at a rate sufficient to avoid removal in the secretion or must colonise normal secretory and/or ductular tissues. More virulent strains of bacteria may resist phagocytic killing despite the presence of large numbers of polymorphonuclear leucocytes. Certain species of bacteria are known to produce haemolytic and/or cytolytic toxins which may have a role in the pathogenesis of the disease.

To date, vaccines to protect the mammary gland from clinical mastitis have attempted to promote more efficient phagocytosis and killing of bacteria (by the production of opsonising antibody) or to inactivate toxic products (by the production of neutralising antibody).

*Streptococcus uberis* is a common cause of bovine mastitis responsible for around 20% of all clinical cases in the UK (Bramley and Dodd 1984). The ability of this organism to infect the lactating mammary gland is dependant on its ability to grow in the secretion and avoid phagocytosis by bovine neutrophils (Leigh et al 1990).

The majority of nitrogen in bovine milk is present in the form of protein (Aston 1975) and, in the absence of proteolysis, bacterial growth in milk is limited by the lack of free amino acids. This is highlighted by the dependence of the lactic streptococci on extracellular, caseinolytic proteinases for growth in milk (Mills and Thomas 1981). The ability of bacteria to grow in mastitic milk is enhanced by the presence of the caseinolytic enzyme plasmin (Marshall and Bramley 1984). The transformation of plasminogen to plasmin requires plasminogen activators which are known to occur in blood plasma and animal tissues (Collen 1980). Certain streptococci are capable of producing streptokinase which activates plasminogen to plasmin but no previously isolated streptokinase activates bovine plasminogen.

According to one aspect of the present invention, there is provided a vaccine for use to treat or prevent a disease in a vertebrate, the vaccine comprising an antigenic entity and a carrier, the antigenic entity being adapted to cause, following vaccination of the vertebrate with the vaccine, an immune response generating antibodies which inhibit a factor from a pathogen which, directly or indirectly, causes breakdown of protein in the vertebrate wherein said breakdown enhances growth of the pathogen.

Antibodies which "inhibit" the factor are those which diminish to a useful extent the ability of the factor to cause the said breakdown of the vertebrate protein. Preferably, for any given interaction between an individual antibody and a molecule of the factor, the said ability is reduced to zero. Suitably, the antibodies are secreted into the environment where the factor acts. Thus, in the case of vaccines against mastitis, the antibodies should be secreted into the milk.

Streptococci are responsible for certain types of dental caries, thus, in the case of dental caries, the antibodies should be secreted into the saliva or present in the mucous membranes associated with the gums and lining of the mouth.

Suitable carriers and adjuvants etc for formulating the antigen entity into a vaccine are known.

Pharmaceutically acceptable carriers may, for example, be liquid media suitable for use as vehicles to introduce the antigenic entity into the vertebrate. An example of such a carrier is saline solution. The antigenic entity may be in solution or suspended as a solid in the carrier.

The vaccine formulation may also comprise an adjuvant for stimulating the immune response and thereby enhancing the effect of the vaccine. Convenient adjuvants for use in the present invention include, for example, aluminium hydroxide and aluminium phosphate.

The vaccines of the present invention may be administered by any conventional method for the administration of vaccines including oral and parenteral (e.g. subcutaneous or intramuscular) injection. The treatment may consist of a single dose of vaccine or a plurality of doses over a period of time.

By "treating or preventing" the disease we mean ameliorating an existing or future disease to a useful extent, and including reducing inflammation to a useful extent.

According to a second aspect of the present invention, there is provided a method of treating or preventing a disease in a vertebrate comprising vaccinating the vertebrate with a vaccine as above.

We believe that the vaccines and methods in accordance with the present invention work by inhibiting a factor from a pathogen which directly or indirectly causes breakdown of protein in the host, such that free amino acids are not generated and the pathogen cannot then grow sufficiently quickly for the disease to persist.

The factor may directly or indirectly activate plasminogen in milk to cause proteolysis of milk proteins. In the case of vaccination against mastitis, the factor may be a bacterial streptokinase capable of activating plasminogen in milk. Suitably, it may be a streptokinase produced by *Streptococcus uberis*. However, streptokinases from other streptococci may also activate plasminogen in milk, for example a streptokinase produced by *Streptococcus dysgalactiae* is a suitable plasminogen activator. Alternatively, the factor may be a bacterial protease capable of causing hydrolysis of milk proteins, for example a *Staphylococcus aureus* protease, a number of which have been reported (see references).

The vaccine of the invention comprises any entity which causes an inhibitory immune response directed to the pathogen's factor discussed above. The entity need not be the whole, native factor. Antigenic fragments may be used, especially those identified by hydrophilicity plots as being hydrophilic, as may modified forms of the factor which are functionally inert, ie they do not cause the breakdown of protein in the host, but which can be used to raise inhibitory antibodies against the factor.

Therefore, when the antigenic entity of the invention is a protein, preferably a bacterial protease, more preferably a streptokinase, the term includes any variants and fragments of the protein which are useful to prepare antibodies which will specifically bind the said protein or mutant forms thereof lacking the function of the native protein. Such variants and fragments will usually include at least one region of at least five consecutive amino acids which has at least 90% homology with the most homologous five or more consecutive amino acids region of the said protein. A fragment is less than 100% of the whole protein.

It will be recognised by those skilled in the art that an antigenic polypeptide of the invention may be modified by known protein modification techniques. These include the techniques disclosed in U.S. Pat. No. 4,302,386 issued 24 Nov. 1991 to Stevens, incorporated herein by reference. Such modifications may enhance the immunogenicity of the antigen, or they may have no effect on such immunogenicity. For example, a few amino acid residues may be changed. Alternatively, the antigenic entity of the invention may contain one or more amino acid sequences that are not necessary to its immunogenicity. Unwanted sequences can be removed by techniques well known in the art. For example, the sequences can be removed via limited proteolytic digestion using enzymes such as trypsin or papain or related proteolytic enzymes.

Alternatively, polypeptides corresponding to antigenic parts of the protein may be chemically synthesised by methods well known in the art. These include the methods disclosed in U.S. Pat. No. 4,290,944 issued 22 Sep. 1981 to Goldberg, incorporated herein by reference.

Peptides may be synthesised by the Fmoc-polyamide mode of solid phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethylacrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivative are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

Thus, when the antigenic entity of the invention is a protein, this includes a class of modified polypeptides, including synthetically derived polypeptides or fragments of the original protein, having common elements of origin, structure, and immunogenicity that are within the scope of the present invention.

Antibodies to the factor may be administered to the host to provide passive immunity, although this will usually be less desirable than immunising with a vaccine of the invention.

According to a third aspect of the present invention there is provided a streptokinase which is capable of activating mammalian plasminogen in milk. Preferably, the streptokinase is or is substantially the same as a streptokinase produced by *Streptococcus uberis*.

A fourth aspect provides a nucleic acid sequence encoding the streptokinase isolated from at least most of the genome sequence in which the sequence is found in nature. In other words the nucleic acid sequence is not claimed in the form in which it has previously existed. Thus, the nucleic acid sequence of the invention includes the nucleic acid sequence when that sequence has been cloned into a bacterial vector, such as a plasmid, or into a viral vector that may be harboured by a bacteriophage provided that such clones are in isolation from clones constituting a DNA library of the relevant chromosome.

It is possible to obtain the nucleic acid sequence that encodes the streptokinase from the amino acid sequence of the streptokinase by utilising methods well known in the art. By using a stretch of amino acid sequence from the protein, specific DNA probes can be synthesised, according to known methods, that will hybridize with the mRNA and DNA encoding the protein.

The gene may comprise the promoter and/or other expression-regulating sequences which normally govern its expression and it may comprise introns, or it may consist of the coding sequence only, for example a cDNA sequence.

The nucleic acid sequence includes any variation which is (i) usable to produce a protein or a fragment thereof which is in turn usable to prepare antibodies which specifically bind to the protein encoded by the said gene or (ii) an antisense sequence corresponding to the gene or to a variation of type (i) as just defined. For example, different codons can be substituted which code for the same amino acid(s) as the original codons. Alternatively, the substitute codons may code for a different amino acid that will not affect the activity or immunogenicity of the protein or which may improve its activity or immunogenicity. For example, site-directed mutagenesis or other techniques can be employed to create single or multiple mutations, such as replacements, insertions, deletions, and transpositions, as described in Botstein and Shortle, "Strategies and Applications of In Vitro Mutagenesis,"*Science,* 229: 193–1210 (1985), which is incorporated herein by reference. Since such modified genes can be obtained by the application of known techniques to the teachings contained herein, such modified genes are within the scope of the claimed nucleic acid sequence.

Moreover, it will be recognised by those skilled in the art that the gene sequence (or fragments thereof) can be used to obtain other DNA sequences that hybridise with it under conditions of high stringency.

Such DNA includes any genomic DNA. Accordingly, the gene of the invention includes DNA that shows at least 55 percent, preferably 60 per cent, and most preferably 70 percent homology with the gene of the invention, provided that such homologous DNA encodes a protein which causes an inhibitory immune response directed to the pathogen's factor as described above.

"Variations" of the gene include genes in which relatively short stretches (for example 20 to 50 nucleotides) have a high degree of homology (at least 50% and preferably at least 90 or 95%) with equivalent stretches of the gene of the invention even though the overall homology between the two genes may be much less. This is because important active or binding sites may be shared even when the general architecture of the protein is different.

Hereinafter, the term "gene" will be used to embrace all such variations and fragments.

The gene or variation thereof may be used, when included in a suitable expression sequence, to prepare an antigenic protein or fragment thereof usable in accordance with the present invention.

A fifth aspect of the invention provides a method of producing the said protein by expressing a corresponding nucleic acid sequence in a suitable host cell or by amino acid synthesis.

Thus, the nucleic acid of the invention may be used in accordance with known techniques, appropriately modified in view of the teachings contained herein, to construct an expression vector, which is then used to transform an appropriate host cell for the expression and production of an antigenic polypeptide of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

The gene of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the gene, preferably as cDNA, is inserted into an expression vector, such as a plasmid, in proper orientation and correct reading frame for expression. If necessary, the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example Aspergillus), plant cells, animal cells and insect cells.

Those vectors that include a replicon such as a procaryotic replicon can also include an appropriate promoter such as procaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical procaryotic vector plasmids are pUC8, pUC9, pBR322 and pBR329 available from Biorad Laboratories, (Richmond, Calif., U.S.A.) and pPL and pKK223 available from Pharmacia, Piscataway, N.J., U.S.A.

A variety of methods have been developed to operatively link DNA to vectors via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities. The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., U.S.A.

The present invention also relates to a host cell transformed with a polynucleotide vector construct of the present invention. The host cell can be either procaryotic or eucaryotic. Bacterial cells are preferred procaryotic host cells and typically are a strain of *E. coli* such as, for example, the *E. coli* strains DH5 available from Bethesda Research Laboratories Inc., Bethesda, Md, U.S.A., and RR1 available from the American Type Culture Collection (ATCC) of Rockville, Md., U.S.A. (No ATCC 31343). Preferred eucaryotic host cells include yeast and mammalian cells, preferably vertebrate cells such as those from a mouse, rat, monkey or human fibroblastic cell line. Preferred eucaryotic host cells include Chinese hamster ovary (CHO) cells available from the ATCC as CCL61 and NIH Swiss mouse embryo cells NIH/3T3 available from the ATCC as CRL 1658.

Transformation of appropriate cell hosts with a DNA construct of the present invention is accomplished by well known methods that typically depend on the type of vector used. With regard to transformation of procaryotic host cells, see, for example, Cohen et al, *Proc. Natl. Acad. Sci. USA*, 69: 2110 (1972); and Sambrook et al, *Molecular Cloning, A Laboratory Manual*, Cold Spring Harbor Laboratory, Cold Spring Harbor, N.Y. (1989). Transformation of yeast cells is described in Sherman et al, *Methods In Yeast Genetics, A Laboratory Manual*, Cold Spring Harbor, N.Y. (1986). The method of Beggs, *Nature,* 275: 104–109 (1978) is also useful. With regard to transformation of vertebrate cells with retroviral vectors containing rDNAs, see, for example, Sorge et al, *Mol Cell. Biol.*, 4: 1730–37 (1984); Graham et al, *Virol,* 52: 456 (1973); and Wigler et al, *Proc. Natl. Acad. Sci. USA,* 76: 1373–76 (1979).

Successfully transformed cells, ie cells that contain a DNA construct of the present invention, can be identified by well known techniques. For example, cells resulting from the introduction of an expression construct of the present invention can be grown to produce the protein of the invention. Cells can be harvested and lysed and their DNA content examined for the presence of the DNA using a method such as that described by Southern, J. Mol. Biol., 98: 503 (1975) or Berent et al, *Biotech.,* 3: 208 (1985). Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium. Preferably, the culture also contains the protein.

Nutrient media useful for culturing transformed host cells are well known in the art and can be obtained from several commercial sources.

A sixth aspect of the present invention provides a vertebrate vaccinated against the host factor. In the case of vaccination against mastitis, the vertebrate is a mammal known to be prone to having mastitis, such as a pig, cow, sheep or horse. At least in the case of these mammals being vaccinated against mastitis by the methods of the invention where the antigen is related to bacterial streptokinase, such mammals can be distinguished from non-vaccinated mammals (even those which have had mastitis) by the presence of neutralising anti-streptokinase antibodies, since the disease does not normally cause a neutralising immune response, at least not as far as streptokinase is concerned.

It is evident that vaccination against mastitis in accordance with the present invention can be used in conjunction with known therapies for mastitis.

The vaccines and methods of the present invention will be discussed and exemplified with specific references to the disease mastitis, the antigenic entity of the vaccine being a streptokinase produced by the causative organism *Streptococcus uberis* or an antigenically equivalent entity. However, the invention relates to a general principle and may be applied to other diseases in which a factor from that pathogen causes breakdown of protein in the host.

Auxotrophic bacteria cannot synthesize certain essential amino acids and these must be provided in the medium for these organisms to grow. The amino acids present in milk are in three forms: free amino acids, non-protein peptides (defined as being soluble in 12% w/v trichloroacetic acid) and polypeptides and proteins. Most amino acids are present in protein form. Bacteria can readily utilise free amino acids and, in some instances, can use amino acids in the form of small peptides. However, to obtain sufficient amino acids to attain high density bacterial growth, or to obtain essential amino acids which only occur in the protein form, auxotrophic bacteria must have a system for proteolysis of milk proteins.

It has been found that *Streptococcus uberis* has a very specific amino acid requirement, as determined by growth studies in a chemically defined medium. These requirements are not met by the amino acids present in the free form in bovine milk, nor by those present in the non-protein nitrogen form in bovine milk (Aston 1975). It is well established that *S. uberis* grows well in the bovine udder: about 300 colony forming units (cfu) infused into the udder result in around $10^5$–$10^7$ cfu/ml milk after 12 hours.

We believe that the vaccines and methods in accordance with the present invention where the antigenic entity is related to bacterial streptokinase work by inhibiting the bacterial streptokinase so that the host's plasminogen is not activated and thus free amino acids are not generated in the milk and growth of the bacteria is thereby inhibited sufficiently quickly for the disease not to persist.

The vaccine may comprise a substantially pure or a non-pure preparation of *Streptococcus uberis* streptokinase. It may also comprise a preparation containing inactivated forms of the streptokinase.

The *S. uberis* streptokinase, or any other plasminogen activating factors or bacterial proteases found to be suitable as vaccines against mastitis, may be administered by various different routes when used as a vaccine. The vaccine is administered so as to produce sufficient antibody in the secretion of the lactating mammary gland to neutralise bacterially-induced proteolysis. This will promote protection of the mammary gland to infection by the bacteria.

Streptokinase produced by *S. uberis* is capable of activating bovine, equine and ovine plasminogen. The streptokinase may be purified from culture filtrates of *S. uberis* by ammonium sulphate precipitation followed by molecular exclusion chromatography. *S. uberis* appears to produce a single protein possessing plasminogen activating activity. The molecular weight of the native molecule is approximately 57 kD, whereas that of the purified protein by SDS PAGE is 29 kD. This suggests that the native molecule consists of a dimer of the 29 kD sub-unit, which is dissociated during electrophoresis in the presence of SDS and 2-mercaptoethanol.

The native molecular weight is distinct from those observed for streptokinase from either Lancefield group A (46.7 kD) or Lancefield group C streptococci (47.2 kD). However, both of these molecules exist as monomeric structures and are not dissociated during SDS PAGE (Huang et al 1989). Staphylokinase, a plasminogen activator from *Staphylococcus aureus*, has a subunit molecular weight of between 23 kD (Jackson and Tang 1982) and 15.3 kD (Sako et al 1982) and has been shown to require a dimeric structure for activity (Jackson et al 1981). This molecule has not been shown to activate bovine plasminogen, and is unlikely to be present in strains of *Staphylococcus aureus* which infect the bovine mammary gland.

*Streptococcus uberis* streptokinase shows some immunological cross reaction with antisera raised to streptokinase from other streptococci, reflecting the presence of similar antigenic sites on the molecules.

A further aspect of the invention provides a process of causing proteolysis in milk comprising adding a streptokinase to the milk whereby the streptokinase activates plasminogen to the caseinolytic protein plasmin.

The importance of plasmin in Swiss-type cheese ripe has been demonstrated (Ollikainen and Kivela 1989). In a study of proteolysis during the ripening of Swiss-type cheese, it was found that the hydrolysis of β-casein by plasmin and the hydrolysis products, __-caseins and protease-peptones, are typical of Swiss-type cheese. The production of __-casein and protease-peptones is indicative of plasmin activity, and it was concluded that plasmin is an important, even essential, enzyme for Swiss-type cheese ripening. Therefore, there is a potential role for streptokinase in the cheese ripening process, where flavour of the final product is dependant upon the presence of peptides, amino acids and their derivatives.

Another potential use of the streptokinase is as a fibrinolytic agent in species which have plasminogen which is susceptible to activation. Other streptokinases are currently used for this procedure in human patients suffering from thrombolytic disorders.

The following examples illustrate preferred aspects of the invention in a non-limiting manner, with reference to the accompanying drawings, in which.

EXAMPLE 1

Purification of Streptokinase from Culture Filtrates

*Streptococcus uberis* strain 0140J was used throughout the present investigation. This strain was originally isolated from a case of bovine mastitis at the National Institute of Dairy Research, Shinfield, Reading, England.

Bacteria were stored at −20° C. in Todd Hewitt broth (THB) containing 25% (w/v) glycerol. Cultures were initially grown for 18 h in 10 ml Todd Hewitt broth at 37° C. A chemically defined medium (Leigh and Field 1991) containing casein hydrolysate (1%, w/v) and glucose (1%, w/v) was inoculated with this culture (10 μl per 500 ml medium) and incubated at 37° C. for 18 h. The cells were removed by centrifugation (10,000 g; 20 min) and filtration (0.45 μm pore size) of the resulting supernatant. Sodium azide was added to the culture filtrate to a final concentration of 0.05% (w/v).

The purification of streptokinase from culture filtrates may also be achieved by an affinity chromatography system using immobilised monoclonal antibodies. (Harlow, E. & Lane, D. (1988) Antibodies. A laboratory manual. Cold Spring Harbour (U.S.A.).)

Ammonium sulphate precipitation from culture filtrates, gel filtration and detection of streptokinase activity

*Streptococcus uberis* strain 0140J was used. Saturated ammonium sulphate solution was added to the cell-free culture filtrate to a final concentration of 38% (v/v). The mixture was stirred at 4° C. for 20 h and the resulting precipitate collected by filtration (0.45 μm pore size).

The precipitate was redissolved in 100 ml of distilled water containing 0.05% (w/v) sodium azide and dialysed for 24 h against 2.0 l of the same diluent. The dialysate was concentrated ten fold in a stirred pressure cell (Amicon, Mass, U.S.A.) using a membrane with 10 kD exclusion limit (Filtron, Mass, U.S.A.).

A column (28×1000 mm) containing Sephadex G-75 (Pharmacia, Uppsala, Sweden) with an approximate packed bed volume of 500 ml was equilibrated with phosphate buffered saline (PBS) at 4° C. Approximately 10 ml of the ammonium sulphate precipitated, redissolved, dialysed and concentrated protein solution was applied to the column and proteins eluted in PBS at a flow rate of 0.5–1.0 ml/min. Fractions (10 ml) were collected and 5 μl of each assayed for bovine plasminogen activating activity.

Preliminary experiments demonstrated that streptokinase activity was precipitated from cell-free culture filtrates by ammonium sulphate at a concentration of 33–38% saturation (data not shown). A concentration of 38% saturation was subsequently used for the precipitation of streptokinase from 2.5 l of cell-free culture filtrate. The precipitate was redissolved, dialysed and concentrated prior to gel filtration.

Figure 1:
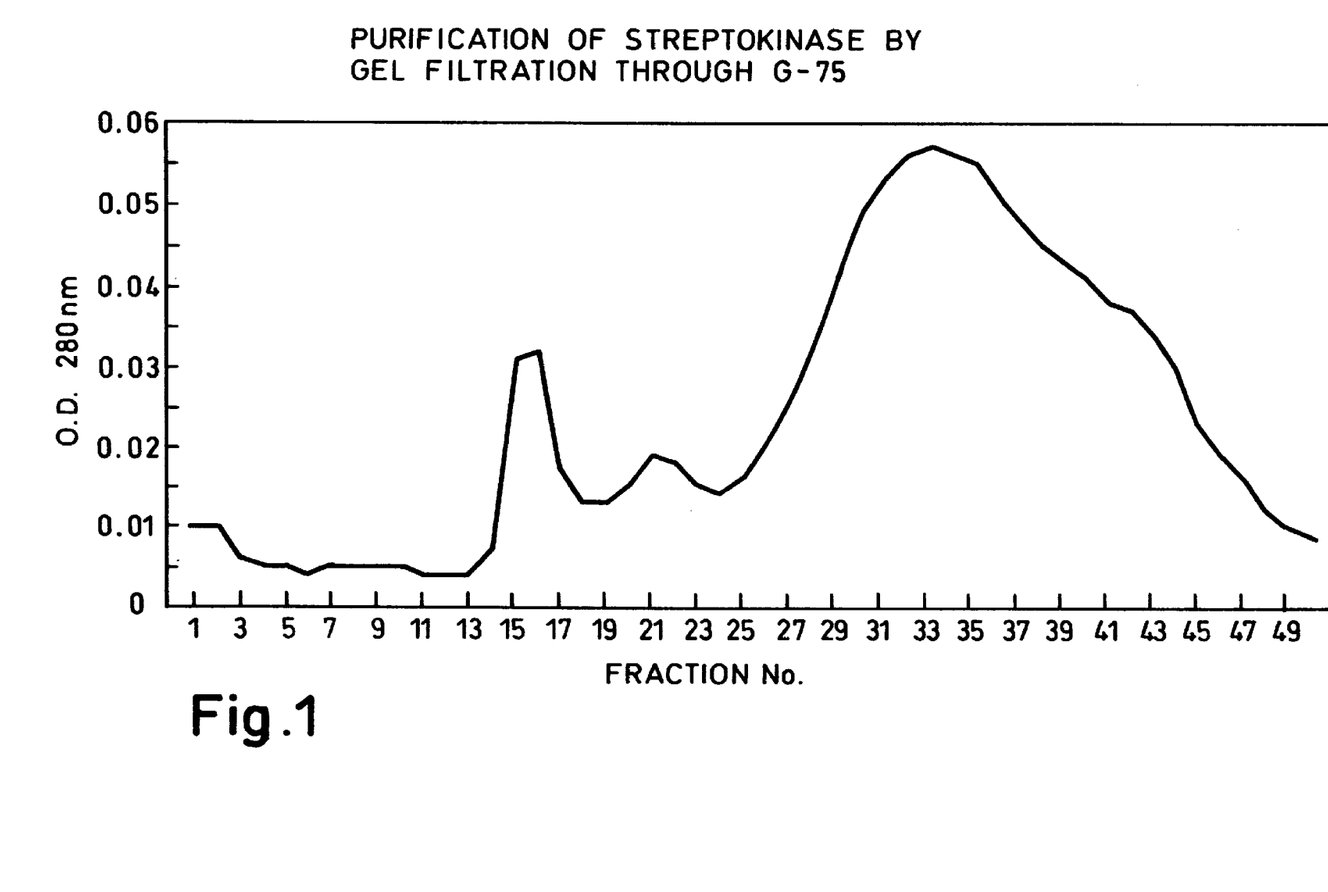
FIG. 1 illustrates an elution profile of ammonium sulphate precipitated proteins from culture filtrate of *Streptococcus uberis*.

The streptokinase activity eluted from the G-75 column as a single active peak with an apparent molecular weight of approximately 57 kD (FIG. 1). Fractions 21 and 22 were pooled (high purity streptokinase) as were fractions 19, 20, 23 and 24 (low purity streptokinase) and stored at −70 C with no apparent loss of activity.

Sodium dodecyl sulphate polyacrylamide gel electrophoresis (SDS PAGE) and protein staining The purity of the pooled fractions containing streptokinase activity was determined using the SDS PAGE and protein staining technique previously described.

Figure 2:
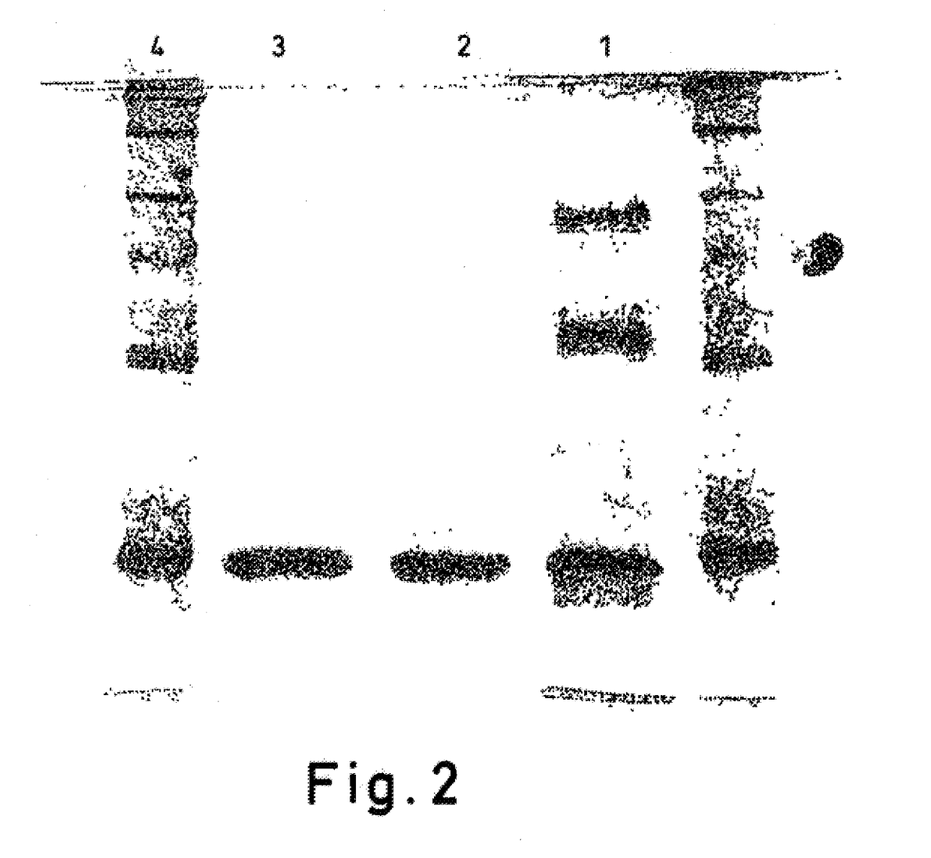
FIG. 2 illustrates the separation of ammonium sulphate precipitated proteins and high streptokinase activity fractions from molecular exclusion chromatography. Ammonium sulphate precipitated proteins (1). Low purity fraction (2). High purity fraction (3). Prestained molecular weight standards (Sigma) with native molecular weights of 180, 116, 84, 58, 48.5, 36.5 and 26.6 kD (4).

The redissolved, dialysed and concentrated ammonium sulphate precipitate contained 6 proteins with molecular weights ranging from 100 to 29 kD. The low purity fractions contained the 29 kD protein and trace amounts of the others whereas the high purity fractions contained only a single band with a molecular weight of 29 kD (FIG. 2).

EXAMPLE 2

Detection of Plasminogen Activation by Agarose/ Skimmed Milk Overlay

Plasminogen from rabbit, human, porcine, equine and bovine plasma was obtained from Sigma Chemical Co. (Poole, Dorset, UK) and reconstituted in sterile distilled water to a final concentration of 1.0 unit ml$^{-1}$. Streptokinase from a Lancefield group C Streptococcus was also obtained from Sigma, reconstituted at a concentration of 1 mg ml$^{-1}$ in phosphate buffered saline (pH 7.4). Plasminogen and streptokinase were stored at −70° C. and thawed only once prior to use.

Overnight cultures in THB were streaked onto Todd Hewitt agar and incubated at 37° C. for 18 h. Plates with isolated colonies were overlaid with 10 ml of molten agarose (10 μml$^{-1}$) containing NaCl (150 mM), Tris/HCl (50 mM, pH 8.1), Oxoid skimmed milk (1 μl % v/v) and bovine plasminogen (10 μg ml$^{-1}$) and incubated at 37° C. Controls were performed using overlays identical to that above except that plasminogen was omitted.

Figure 3A:
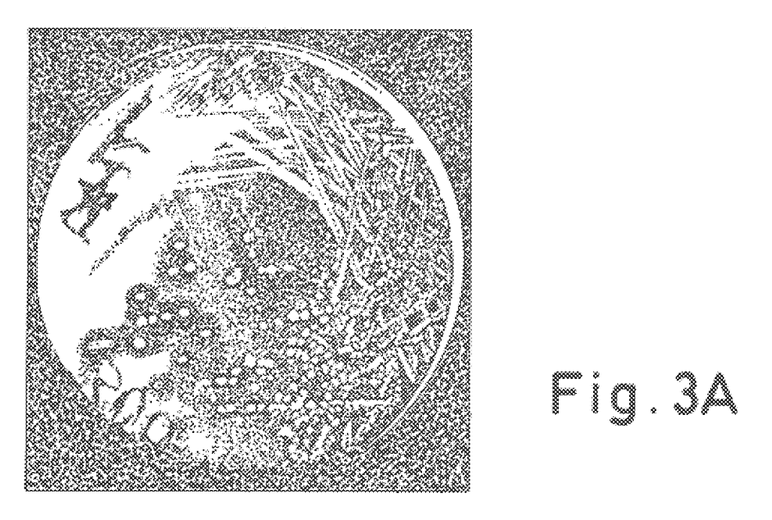
FIG. 3A and 3B illustrates the hydrolysis of milk proteins by *Streptococcus uberis* in the presence and absence of bovine plasminogen. *Streptococcus uberis* strain 0140J (A and B) overlaid with agarose containing skimmed milk in the presence (A) and absence (B) of bovine plasminogen.
Figure 3B:
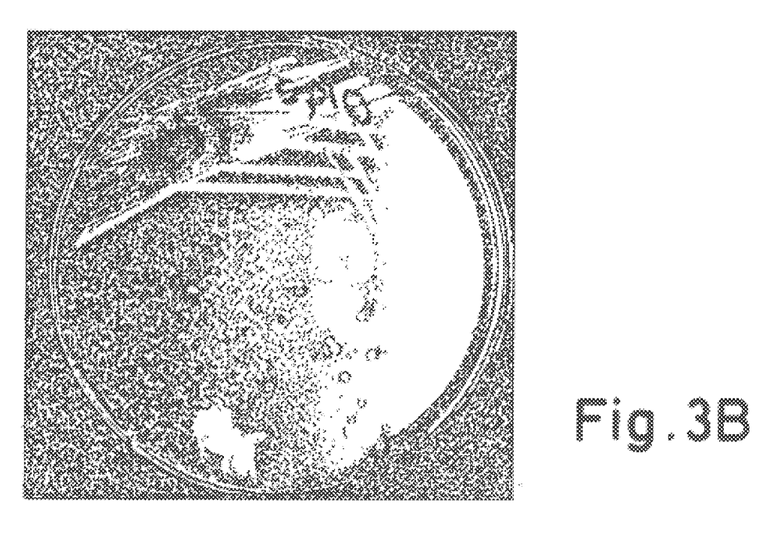

All five strains of S. uberis (0140J, EF20, ST10, C216, C197C) produced zones of caseinolytic activity in skimmed milk, bovine plasminogen, agarose overlays within 4 hours at 37° C. (FIG. 3A). There may be some strains of S. uberis, however, which do not produce this activity: these will probably show reduced virulence for the bovine mammary gland. No zones were detectable around isolated colonies in overlays in the absence of bovine plasminogen (FIG. 3B).

EXAMPLE 3

Plasminogen Activation and detection of Plasmin

Figure 4:
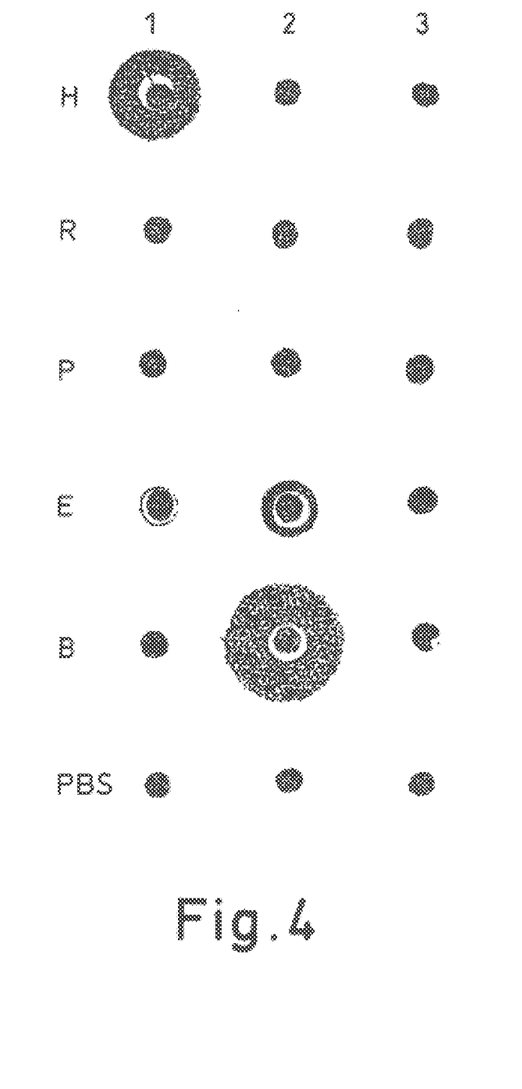
FIG. 4 illustrates the detection of caseinolytic activity following activation of plasminogen with streptokinase from a Lancefield group C streptococcus or *S. uberis* culture filtrate. Wells contain a mixture of streptokinase from a Lancefield group C Streptococcus (column 1), *S. uberis* culture filtrate (column 2), or phosphate buffered saline (column 3) and either human (row H), rabbit (row R), porcine (row P), equine (row E) or bovine (row B) plasminogen. The row labelled PBS contained phosphate buffered saline in place of plasminogen.

Equal volumes of plasminogen (1.0 unit ml–$^1$ from a variety of mammalian species) and S. uberis culture filtrate or streptokinase (1 μ g ml–$^1$) from a Lancefield group C Streptococcus were mixed and incubated at 37° C. for 45 min after which 10 μl pI was assayed for the presence of plasmin by the detection of caseinolytic activity. Activity was detected by diffusion from wells cut in skimmed milk agarose (as overlays above containing no plasminogen) following 24 h incubation at 37°C. (FIG. 4).

Culture filtrates from S. uberis activated bovine and equine plasminogen but the activity with the latter was only apparent after incubation of the skimmed milk agarose for around 18 h compared to 2 h when using bovine plasminogen. This suggests either a lower activity of S. uberis streptokinase for this substrate or the poor activity of the resulting plasmin molecule for bovine milk proteins. S. uberis culture filtrate failed to activate plasminogen from human, rabbit or pig. In contrast, streptokinase from the Lancefield group C Streptococcus activated human plasminogen and showed a trace of activity towards equine plasminogen but no activity towards that from rabbit, bovine or porcine plasma. Neither S. uberis culture filtrate nor streptokinase from the Lancefield group C Streptococcus showed any caseinolytic activity in the absence of plasminogen.

Thus, the streptokinase activity present in S. uberis culture filtrate differed from that isolated from Lancefield group E streptococci which is reported to activate porcine plasminogen (Ellis and Armstrong 1971); S. uberis culture filtrate failed to activate this molecule (FIG. 4). It also differed from similar activities from S. equisimilis and S. pyogenesboth of which activate human but not bovine plasminogen (Castellino 1979, Wulf and Mertz 1969) whereas streptokinase from S. uberis activates bovine but not human plasminogen. This is the first report of 15 the presence of plasminogen activating activity in S. uberis and the first report of a streptokinase which activates bovine plasminogen.

EXAMPLE 4

Figure 5:
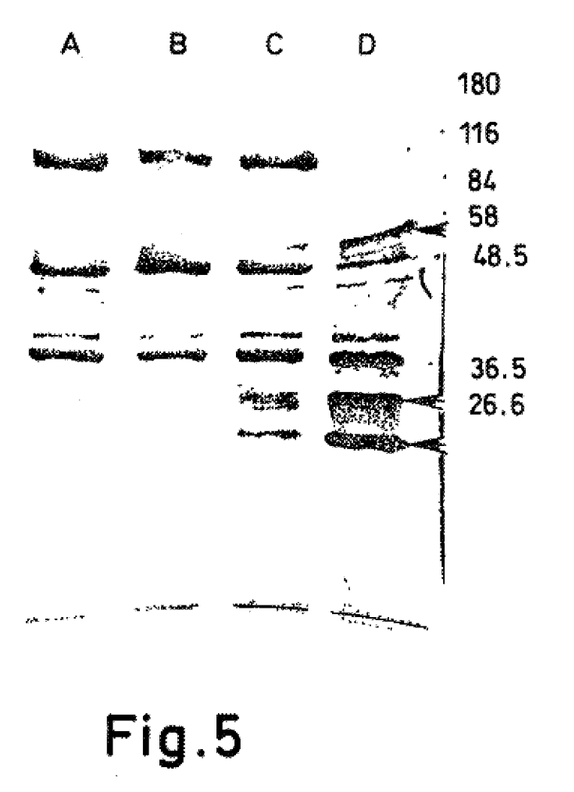
FIG. 5 illustrates SDS PAGE of bovine plasminogen following incubation in the presence of *S. uberis* culture filtrate. Tracks of bovine plasminogen in the presence of 2 μl of phosphate buffered saline (A), *S. uberis* culture filtrate diluted 1/1000 (B), 1/100 (C) and 1/10 (D) in phosphate buffered saline (PBS). Arrows indicate the position of the plasmin associated polypeptides. No protein bands were detected following electrophoresis of culture filtrate diluted ⅕ in PBS. Numbers indicate the position of proteins of known molecular weight.

Conversion of Plasminogen to Plasmin and Detection by Polyacrylamide Gel Electrophoresis and Protein Staining Bovine plasminogen (0.005 unit in a volume of 5 μl) was mixed with 2 μof S. uberis culture filtrate and incubated at 37°C. for 1 h. Samples were mixed with an equal volume of sample-buffer containing sodium dodecyl sulphate (0.01% w/v) and 2-mercaptoethanol (0.2% v/v) and heated at 65° C. for 5 min. Proteins were separated by electrophoresis (Laemmli 1970) and detected by the staining procedure of Oakley et al (1980) (FIG. 5).

The plasminogen used during this investigation contained contaminating proteins. The suppliers claim the plasmin contamination to be less than 5% total protein (Sigma Chemical Co, Poole, UK). Bovine plasminogen had an apparent molecular weight of 91.2 kD and this agrees with the calculated molecular weight based on the amino acid sequence of this protein (Schaller et al 1985). Activation of plasminogen was achieved after 60 min by a 1/10 dilution of S. uberis culture filtrate (FIG. 5). This resulted in the loss of the 91.2 kD protein band together with another protein (48.5 kD). It is not clear whether the disappearance of the 48.5 kD protein was a result of the action of the culture filtrate or of the resulting plasmin activity. The disappearance of these two proteins corresponded with the formation of three smaller polypeptides with apparent molecular weights of 56.2, 28.8 and 25.4 kD.

Activation of bovine plasminogen by urokinase (a plasminogen activator of human origin) is predicted to result in the formation of only two polypeptides with molecular weights of 53.7 and 25.4 kD (Schaller et al 1985). These probably correspond to the proteins at 56.2 and 25.4 kD, respectively. The predicted 53.7 kD polypeptide contains two potential glycosylation sites (Schaller et al 1985) and this might account for the discrepancy between the predicted and the observed values. This suggests that the S. uberis streptokinase acts in a similar fashion to urokinase during the activation of the bovine plasminogen molecule.

Since no protein bands were seen following electrophoresis of culture filtrate at a concentration two fold higher than that used to achieve total plasminogen activation, the presence of an additional polypeptide (28.8 kD) cannot be explained simply by the presence of bacterial proteins. The cumulative total of the molecular weights of the three polypeptides observed following plasminogen activation during this investigation shows a significant discrepancy from that of bovine plasminogen. One possible explanation for this is that the 28.8 kD polypeptide is a product of the degradation of the 48.5 kD protein which contaminates the plasminogen preparation and is depleted during activation. The determination of the molecular weights of the products of the activation of purified plasminogen by purified S. uberis streptokinase will resolve this discrepancy.

EXAMPLE 5

Production of Monoclonal Antibodies to S. uberis Streptokinase

Vaccination of mice

Purified streptokinase (10 μ l g) was mixed with Freund's incomplete adjuvant and injected subcutaneously into Balb/c mice. This procedure was repeated after an interval of approximately 21 days.

Production of specific antibody was monitored 10 days after the second injection, as described below. Approximately 1 month following the second injection and 4 days prior to fusion of spleen cells (see below) antibody production was boosted by intravenous administration of 10 μg of purified streptokinase suspended in phosphate buffered saline (PBS; pH 7.2).

Production and cultivation of hybridoma cells

Spleens were removed from vaccinated mice and fusions carried according to standard methods (Galfre et al, 1977).

Fused cells were resuspended in HAT medium (RPMI 1640 (Gibco BRL, Life Technologies, Paisley, UK) containing 10% (v/v) foetal bovine serum, 0.1 mM hypoxanthine, 0.016 mM thymidine and 40 $\mu$M aminopterin Sigma, Poole, UK)). Cells were then dispensed at a concentration of $2 \times 10^6$ cells/ml into 24-well cluster plates (1 ml/well) which had been seeded 24 h previously with 1 ml HAT medium containing $2 \times 10^4$ murine macrophages. The plates were incubated at 37° C. in the presence of 5% $CO_2$ until hybridoma colonies were clearly visible when samples of the supernatants were 2 0 tested for the presence of streptokinase specific antibody. Colonies from which the supernatant showed streptokinase specific antibody were grown up and supernatants tested for anti-streptokinase activity as before, cultures showing activity were cloned twice by limiting dilution.

Ascitic fluid was prepared by intra peritoneal (I.P.) injection of Balb/c mice with $2-4 \times 10^6$ cloned hybridoma cells. The mice had been given an I.P. injection of 0.5 ml "Pristane"(a trademark of the Aldrich Chemical Co, Gillingham, UK) one week prior to this procedure.

Detection of streptokinase specific murine antibody

Purified, lyophilised streptokinase was redissolved in sodium carbonate buffer (pH 9.6) at a concentration of 1 $\mu$g/ml and 100 $\mu$l was added to wells of a flat-bottomed, 96-well micro-titre tray (Flow labs (Linbro), Virginia, USA). Streptokinase was allowed to bind to the wells for 18 h at 4° C. Unbound streptokinase was removed from the wells by washing with excess ELISA-buffer (0.1 M sodium phosphate buffer, pH 7.2 containing tween-20, 0.05% v/v). Antibody containing solutions were added to appropriate wells and allowed to react with the bound streptokinase for 1 h at 37° C. Unbound antibody was removed by washing with ELISA-buffer, as before. Bound antibody was detected by addition of a murine immunoglobulin-specific antibody conjugated to horse radish peroxidase (HRP), incubation for 1 h at 37° C. and removal of unbound conjugate by washing in ELISA-buffer. This was followed by colorimetric detection of the bound HRP by the addition of 100 $\mu$l of citrate buffer (24.3 ml of 0.05M citric acid and 25.7 ml of 0.1M $Na_2HPO_4$) containing 0-phenylaminediamine (0.34 mg/ml) and hydrogen peroxide (0.03%, v/v). Colour development was allowed to proceed for approximately 20 min and was stopped by the addition of an equal volume of 1M sulphuric acid.

The colour was measured spectrophotometrically at a wavelength 15 of 492 nm and the presence of specific antibody determined by comparison with the colour development in control wells (wells which did not contain streptokinase and others to which the antibody containing solution had not been added).

Detection of streptokinase neutralising activity

Monoclonal antibodies (mAbs) were diluted in PBS (pH 7.2), and each dilution mixed with an equal volume of streptokinase (0.5 $\mu$ g/ml). The mixtures were incubated at room temperature for 10 min after which 20 $\mu$ l from each dilution of each mAb was placed into a well cut into a sheet of agarose (1% w/v in PBS) containing Oxoid skimmed milk (1%, w/v) and $10^{-3}$ units/ml of bovine plasminogen (Sigma).

Wells containing mAb and streptokinase were compared to control wells to which streptokinase and an equal volume of PBS had been added (positive) and those to which mAb alone had been added (negative). The ability of mAbs to neutralise streptokinase is expressed as the lowest concentration at which total inhibition of 0.5 $\mu$ g/ml was achieved (Table 1).

TABLE 1

Comparison of the neutralising activity of streptokinase specific monoclonal antibodies.

| MONOCLONAL ANTIBODY (Fusion No. Code No.) | INHIBITORY CONCENTRATION ($\mu$g/ml) |
|---|---|
| F429.EC3 | 22 |
| F429.FG8 | 100 |
| F449.ED1 | >140 |
| F449.DC2 | 23 |
| F450.DA3 | >100 |

EXAMPLE 6

Production of Polyclonal Antibodies to S. uberis Streptokinase

Vaccination of rabbit and detection of specific antibody

Purified streptokinase (50 $\mu$g) was mixed with Freund's incomplete adjuvant, and injected subcutaneously into a New Zealand white rabbit. This procedure was repeated on two further occasions at five and eight weeks after the initial injection. Production of specific antibody was monitored at various times after injection as described for murine antibody in Example 5, except that the antibody conjugated to horse radish peroxidase in this example was specific for rabbit immunoglobulin.

Detection of streptokinase neutralising activity

The ability of immunoglobulin purified from the polyclonal serum using immobilised protein G (MAB TRAP Pharmacia, Uppsala, Sweden) to neutralise streptokinase activity was determined exactly as described in Example 5 for specific monoclonal antibodies.

The polyclonal antibody neutralised the activity of S.uberisstreptokinase but not that from S.equisimilis which was obtained from the Sigma Chemical Co. (Poole, Dorset UK)

REFERENCES

Aston, J. W. (1975) Free amino acids in milk. Their determination by gas-liquid chromatography and their variation due to mastitic infection. *Australian Journal of Dairy Technology* 30, 55–59.

Benslimane, S., M. J. Dognin-Bergeret, J. L. Berdague, Y. Gaudemer. (1990) Variation with season and lactation of plasmin and plasminogen concentrations on Motebeliard cows'milk. Journal of Dairy Research 58, 423–435.

Bramley, A. J. and F. H.Dodd. (1978) Reviews of the progress of dairy science. Mastitis control –progress and prospects. *Journal of Dairy Research* 51, 481–512.

Castellino, F. J. (1979) A unique enzyme-protein substrate modifier reaction: plasmin streptokinase interation. *Trends in Biochemical Sciences* 4, 1–5.

Collen, D. (1980) On the regulation and control of fibrinolysis. *Thrombosis and Haemostasis* 43, 77–89.

Ellis, R. P. and Armstrong, C.H. (1971) Production of capsules, streptokinase and streptodornase by Streptococcus group E. *American Journal of Veterinary Research* 32, 349–356.

Galfre, G. et al (1977) Antibodies to major histocompatibility antigens produced by hybrid cell lines. Nature 266, 550–552.

Hill, A. W. and Leigh, J. A. (1989) DNA fingerprinting of *Streptococcus uberis* : a useful tool for the epidemiology of bovine mastitis. Epidemiology and Infection 103, 165–171.

Huang, Malke and Ferritti (1989) The streptokinase gene of group A streptococci: cloning, expression in *Escherichia coli,* and sequence analysis. *Molecular Microbiology* 32, 197–205.

Jackson, Esmon and Tang (1981) Streptokinase and staphylokinase. In: *Methods in Enzymology.* Lorand (ed). 80, 387, Academic Press, New York.

Jackson and Tang (1982) Complete amino acid sequence of streptokinase and its homology with serine proteases. *Biochemistry* 21, 6620–6625

Laemmli, U. K. (1970) Cleavage of structural proteins during the assembly of the head protein of bacteriophage T4. *Nature* 277, 680–685.

Leigh, J. A., Field, T. R. and Williams, M. R. (1990) Two strains of differing ability to cause clinical mastitis, differ in their ability to resist some host defence factors. *Research in Veterinary Science* 49, 85–87.

Leigh, J. A., Field, T. R. (1991) Killing of *Streptococcus uberis* by bovine neutrophils following growth in chemically defined media. *Veterinary Research Communications* 15,1–6.

Malke and Feretti (1984) Streptokinase: Cloning, expression and excretion by *Escherichia coli. Proceedings of the National Academy of Sciences.*USA. 81, 3557–3561.

Malke, Roe and Ferretti (1987) In: *Streptococcal Genetics.* Ferretti and Curtis III (eds). 286, American Society for Microbiology. Washington D.C.

Mills, O. E. and Thomas, T. D. (1981) Nitrogen sources for growth of lactic streptococci in milk. *New Zealand Journal of Dairy Science and Technology* 15,43–55.

Oakley, B. R., Kirsch, D. R. and Morris, R.N. (1980) A simplified ultrasensitive silver stain for detecting proteins in polyacrylamide gels. *Analytical Biochemistry* 105, 361–363.

Schaller, J., Moser, P. W., Dannegger-Muller, G. A. K, Rosselet, S. J., Kampher, U. and Rickli, E. E. (1985) Complete amino acid sequence of bovine plasminogen. Comparison with human plasminogen. *European Journal of Biochemistry* 149, 267–278.

Wulf, R. J., and Mertz, E. T., (1969) Studies on plasminogen VIII. Species specificity of streptokinase. *Canadian Journal of Biochemistry* 47, 927–22.

Marshall, V. M. and Bramley, A. J. (1984) Stimulation of *Streptococcus thermophilus* growth in mastitic milk. *Journal of Dairy Research* 51, 17–22.

Arvidson, S. (1973) Studies on extracellular proteolytic enzymes from *Staphylococcus aureus* II. Isolation and characterisation of an EDTA-sensitive protease. Biochim. Biophys. Acta 302: 149–157.

Arvidson, S., Holme, T., Lindholm, B. (1972) The formation of extracellular proteolytic enzymes by *Staphylococcus aureus.* Acta. Path. Microbiol. Scand. 80: 835–844.

Arvidson, S., Holme, T., Lindholm, B (1973) Studies on extracellular proteolytic enzyme from *Staphylococcus aureus*: I. Purification and characterisation of one neutral and one alkaline protease. Biochem. Biophys. Acta. 301: 135–148.

Beaudet, R., Saheb, S.A., Drapeau, G.R. (1974) Structural heterogeneity of the protease isolated from several strains of *Staphylococcus aureus.* J. Biol. Chem. 249: 6468–6471.

Bjorklind, A & Arvidson S., (1977) Occurrence of an extracellular serine protease among staphylococcal strains. Acta. Path. Microbiol. Scand. 85: 277–280.

Carmona, C & Gray, G.L. (1987) Nucleotide sequence of the serine protease gene of *Staphylococcus aureus* strain V8. Nuc.Acid. Res. 15: 6757.

Drapeau, G. R. (1978) The primary structure of staphylococcal protease. Can J. Biochem. 56: 534–544.

Drapeau, G. R., Boily, Y. & Houmard, J. (1972) Purification and properties of an extracellular protease of *Staphylococcus aureus.* J. Biol. Chem. 247: 670–6726.

Potempa, J., Dubin, A., Korzus, G. & Travis, J. (1988) Degradation of elastin by a cysteine proteinase from *Staphylococcus aureus.* J. Biol. Chem. 263: 2664–2667.

Ryden, A-C., Ryden, L. & Philipson, L. (1974) Isolation and properties of a staphylococcal protease preferentially cleaving glutamoyl-peptide bonds. Eur. J. Biochem. 44: 105–114.

Saheb, S. A. (1976) Purification et characterisation d'une protease extracellulaire de *Staphylococcus aureus* inhibee par l'EDTA. Biochemie. 58: 793–804.

I claim:

1. A vaccine for use to treat or prevent mastitis in a bovine species, comprising an immunologically effective amount of a plasminogen-activating streptokinase protein produced by *Streptococcus uberis*, and a pharmaceutically acceptable carrier.

2. A vaccine composition for use to treat or prevent mastitis in a bovine species, comprising a plasminogen-activating streptokinase protein produced by *Streptococcus uberis*, and a pharmaceutically acceptable carrier.

3. A method of treating or preventing mastitis in a bovine species, comprising vaccinating a cow with an immunologically effective amount of a plasminogen-activating streptokinase protein produced by *Streptococcus uberis*, and a pharmaceutically acceptable carrier.

4. An isolated plasminogen-activating streptokinase protein produced by *Streptococcus uberis*,or an immunogenic fragment thereof.

* * * * *